(12) United States Patent
Khatib

(10) Patent No.: US 9,289,399 B2
(45) Date of Patent: Mar. 22, 2016

(54) OPHTHALMOLOGIC COMPOSITIONS AND USE MODE THEREOF

(75) Inventor: Walid Khatib, Ville di Pietrabugno (FR)

(73) Assignee: LABORATOIRES THEA (FR)

( * ) Notice: Subject to any disclaimer, the term of this patent is extended or adjusted under 35 U.S.C. 154(b) by 420 days.

(21) Appl. No.: 13/464,524

(22) Filed: May 4, 2012

(65) Prior Publication Data

US 2012/0220637 A1 Aug. 30, 2012

Related U.S. Application Data

(62) Division of application No. 11/908,161, filed as application No. PCT/FR2006/000528 on Mar. 9, 2006, now abandoned.

(30) Foreign Application Priority Data

Mar. 9, 2005 (FR) ...................... 05 02357

(51) Int. Cl.
| | |
|---|---|
| A61K 31/44 | (2006.01) |
| A61K 31/137 | (2006.01) |
| A61K 9/00 | (2006.01) |
| A61K 31/167 | (2006.01) |
| A61K 31/4409 | (2006.01) |
| A61K 31/445 | (2006.01) |
| A61K 45/06 | (2006.01) |

(52) U.S. Cl.
CPC ............. *A61K 31/137* (2013.01); *A61K 9/0048* (2013.01); *A61K 31/167* (2013.01); *A61K 31/44* (2013.01); *A61K 31/445* (2013.01); *A61K 31/4409* (2013.01); *A61K 45/06* (2013.01)

(58) Field of Classification Search
None
See application file for complete search history.

(56) References Cited

U.S. PATENT DOCUMENTS

| 3,026,323 | A | 3/1962 | Schacter | |
|---|---|---|---|---|
| 5,779,661 | A | 7/1998 | Stephen et al. | |
| 6,218,428 | B1 | 4/2001 | Chynn | |
| 2004/0013729 | A1 | 1/2004 | Buono | |
| 2004/0072809 | A1* | 4/2004 | Demopulos et al. | 514/171 |

FOREIGN PATENT DOCUMENTS

| WO | 9717989 A1 | 5/1997 |
|---|---|---|
| WO | 0134088 A2 | 5/2001 |

OTHER PUBLICATIONS

Apt et al (Am J Ophthalmology 89:553-559, 1980; Abstract only).*
Paganelli, et al.; "A Single Intraoperative Sub-Tenon's Capsule Triamcinolone Acetonide Injection for the Treatment of Post-Cataract Surgery Inflammation"; American Academy of Ophthalmology; pp. 2102-2108.
Marchini, et al.; "Comparative Study of the Effects of 2% Ibopamine, 10% Phenylephrine, and 1% Tropicamide on the Anterior Segment"; Investigative Ophthalmology & Visual Science; Jan. 2003; pp. 281-289.
Behndig, et al.; "Evaluation of Surgical Performance with Intracameral Mydriatics in Phacoemulsification Surgery"; Acta Ophthalmol Scand 2004; pp. 144-147.
Husarova; "Functional State of the Ciliated Epithelium Under the Effect of Aerosol Ephatin"; 1976; pp. 67-69 (1 page abstract only).
Lundberg, et al.; "Intracameral Mydriatics in Phacoemulsification Cataract Surgery"; J Cataract Refract Surg 2003; pp. 2366-2371.
International Search Report; Application No. PCT/FR2006/000528; Issued: Jun. 1, 2006; Mailing Date: Jun. 21, 2006; 5 pages.
Mathalone, et al.; "Long-term Intraocular Pressure Control After Clear Corneal Phacoemulsification in Glaucoma Patients"; J Cataract Refract Surg 2005; pp. 479-483.
Black, et al.; "Necessity of the Honan Intraocular Pressure Reducer in Cataract Surgery Using Topical Anesthesia"; J Cataract Refract Surg—vol. 25, Feb. 1999; pp. 223-226.
Reah, et al.; "Peribulbar Anaesthesia Using a Mixture of Local Anaesthetic and Vecuronium"; 1998 Balckwell Science Ltd; pp. 551-554.
Apt, et al.; "Pupillary Dilatation with Single Eyedrop Mydriatic Combinations"; American Journal of Ophthalmology; pp. 553-559; 1980.
Miller, et al.; "Systemic Reaction to Subconjunctival Phenylephrine"; Canad. J. Ophthal. 13:291 1978; pp. 291-293.
Keembiyage, et al.; "Tachycardia and Myocardial Ischaemia Following Subconjunctival Injection of Mydricaine (No. 02) for Vitrectomy Procedure"; Clinical & Experimental Ophthalmology; Feb. 2005, vol. 33, No. 1; pp. 105-106.
Mather, et al.; "The Effect of Cataract Surgery on Ocular Levels of Topical Moxiflozacin"; 2004 Elseiver Inc, All rights reserved; pp. 554-559.
Ong-Tone; "Use of a Wick to Deliver Preoperative Mydriatics for Cataract Surgery"; J Cataract Refract Surg 2003; 29: pp. 2060-2062 ASCRA and ESCRS.

* cited by examiner

*Primary Examiner* — Craig Ricci
(74) *Attorney, Agent, or Firm* — St. Onge Steward Johnston & Reens, LLC

(57) ABSTRACT

The invention concerns a pharmaceutical composition characterized in that it contains a combination of a parasympatholytic agent, a sympathomimetic agent and a local anaesthetic. Such a composition may be injected into the anterior chamber of the eye before a cataract operation or instilled on the eye before laser treatment.

8 Claims, No Drawings

OPHTHALMOLOGIC COMPOSITIONS AND USE MODE THEREOF

CROSS-REFERENCE TO RELATED APPLICATIONS

The present Application is a Division of U.S. patent application Ser. No. 11/908,161 filed Sep. 10, 2007, currently pending, which is the National Stage of International Patent Application PCT/FR2006/000528 filed Mar. 9, 2006 which designates the United States and claims priority from French Patent Application 0502357 filed Mar. 9, 2005.

FIELD OF THE INVENTION

The present invention concerns the therapeutic field and more particularly the ophthalmologic field.

It more particularly deals with new pharmaceutical compositions for the treatment of pain and/or lesions of the eye during surgical or physical operations or prior to an operation on the eye.

BACKGROUND OF THE INVENTION

Its subject is more precisely compositions based on a parasympatholytic agent, an adrenergic substance and advantageously a local anaesthetic, in the context of pre-operative treatment of the eye for a surgical operation on cataracts or laser treatment of the retina. These active ingredients are to be administered simultaneously on or in the eye.

According to a particularity of the invention, the parasympatholytic agent is a mydriatic agent and preferably a derivative of tropic acid such as a tropic acid ester or a tropic acid amide or a cyclohexyl or cyclopentylacetic acid amide.

Among these parasympatholytic agents, we shall notably mention cyclodrine, eucatropine, homatropine as well as atropine (benzylic ester of tropic acid), N-methyl hyoscine and especially tropicamide (N-ethyl 2-phenyl N-4 pyridyl methyl hydracrylamide or pyridyl methyl benzene acetamide).

Among the local anaesthetics, we shall more particularly mention butocaine, prilocaine, procaine, novocaine, tetracaine, ambucaine, amylocaine, bupivacaine, carticaine, butoxycaine, formocaine, mepivacaine, etidocaine, prilocaine, orthocaine, oxybuprocaine or benoxinate, and mainly lidocaine or diethylamino 2,6 dimethyl acetanilide, or one of its salts.

Among the adrenergic substances, we shall more particularly mention noradrenaline, phenylephrine, isoprenaline, dipivefrine, dimetrophine, norfenefrine, pholedrine or octedrine.

Combinations of this type have already been described in the literature.

Notably, the publication by Behndig A et al. (Acta Ophthalmologica Scandinavica (2004) 82(2) 144-147) describes the use of a composition containing 0.1% cyclopentolate, 1.5% phenylephrine and 1% lidocaine, designed for intracameral administration in the context of a surgical operation by phacoemulsification.

In this publication, the results obtained by intracameral injection of mydriatics were compared with those obtained by topical application. The effects, and especially the side effects, are no different. It appears to be important with this technique to avoid the general effects related to the administration of epinephrine or the intracameral administration of lidocaine.

Another publication (L. Apt et al. Am J. of Ophthalmology 89(4) (1980) 553-559) describes the use of ophthalmologic compositions containing tropicamide (0.5% or 1%) or cyclopentolate (0.5%) combined with phenylephrine at 2.5%, in instillation in the eye, one drop in each eye. In certain cases, instillation of the combination of two mydriatic agents is preceded by topical application of a drop of the anaesthetic proparacaine at 0.5%. The combination of three active ingredients is not envisaged, however.

Furthermore, S. A. Miller and W. F. Mieler have demonstrated (Canad. J. Ophtal 13 (1978) 291-293) the systemic effects resulting from subconjunctival injection of a combination of phenylephrine at a very high concentration (3.3%), cocaine (local anaesthetic at 1.3%) and atropine (0.3%), notably leading to an increase in blood pressure. This increase was followed by hypotension, pulmonary oedema and endocardial ischemia. The authors conclude by insisting on the dangerous effects on blood pressure of phenylephrine applied to the eye.

These triple combinations, notably the use of cyclopentolate as a parasympatholytic agent, at the concentrations indicated, are excluded from this invention.

These references, considered as the most similar in the prior art, show the need to effectively combine strong pharmacological action and nearly total absence of general effects resulting from the resorption in the eye of drugs having systemic effects.

SUMMARY OF THE INVENTION

The compositions according to the invention are of major interest, notably in intracameral injection, for preparing the eye before a surgical operation or during the surgical operation, notably in the surgical treatment of cataracts. As the volume of the intracameral chamber does not exceed 300 µl in man, the volume of the composition injected should preferably be less than or equal to 200 µl, notably between 50 and 200 µl.

The compositions according to the invention can also be administered in a collyrium beforehand or during a laser intervention on the retina. Typically, 1 to 5 drops (generally at a volume between 20 and 40 µl) are instilled, which also represents a volume less than or equal to 200 µl.

It is important to point out that the compositions according to the invention are capable of providing very rapid anaesthesia as well as nearly instantaneous, sizeable and sustainable dilation of the pupil for undertaking an examination of the pupil and the surgical operation as quickly as possible. It should also be pointed out that the anaesthesia is of long duration, so that the subject suffers little from the operation they undergo. Such a combination has the advantage of reinforcing the mydriatic effect of the parasympatholytic derivative, but without manifesting an overly long effect which leads to a decrease in vision essentially characterised by prolonged mydriasis. The effects of mydriasis mainly translate into disturbances of vision and balance.

It therefore appeared that the ratios of active ingredients would have to be determined with precision.

The compositions according to the invention can be distinguished from those described in the prior art by a concentration of a sympathomimetic agent, for example phenylephrine, that is sharply reduced. Advantageously, the concentration of the parasympatholytic agent is also reduced.

A combination of just two mydriatic agents is thus distinguished from the solutions in the prior art by low concentrations of sympathomimetic agents, or even parasympatholytic agents.

Advantageously, a composition according to the invention also contains a local anaesthetic agent.

The pharmaceutical compositions according to the invention contain between 0.001 and 0.6% parasympatholytic agent, between 0.04 and 0.5% sympathomimetic agent, and possibly between 0.2 and 3% local anaesthetic agent.

A preferred composition contains between 0.01 and 0.5% parasympatholytic agent defined above, between 0.5 and 1.5% local anaesthetic and between 0.1 and 0.4% sympathomimetic agent.

An ophthalmologic composition according to the invention, highly preferred, contains between 0.015 and 0.025% parasympatholytic agent, advantageously tropicamide, between 0.75% and 1.25% lidocaine and between 0.2 and 0.4% phenylephrine in a single preparation. Such a formulation is particularly well suited to injection into the anterior chamber of the eye before the surgical treatment of cataracts. For this, an incision is made at the time of the operation in the anterior chamber of the eye and the composition is injected into it. This preparation of the eye simultaneously causes mydriasis and local anaesthesia, allowing the later extraction of the lens under favourable conditions. In this precise case, a single injection of a volume of the preparation between 0.05 and 0.2 ml provides the desired effect.

In the case of a laser operation, the concentrations of the pharmaceutical compositions instilled are advantageously adapted. Notably, the concentrations of the parasympatholytic agent and local anaesthetic agent will be significantly higher, in the higher values of the widest range of concentrations. Thus, preferably, the concentrations of the parasympatholytic agent will be between 0.1 and 0.25% and the concentration of the local anaesthetic agent will be between 2 and 3%. Such preparations being designed for a single use, the use of a preservative may not be necessary. The preparations according to the invention therefore may not contain any preservatives. In this situation, the method of administration may also be different, proceeding with the instillation of the preparation on the treated eye in two to four times at one minute intervals. Thus, sedation of pain is ensured more immediately and for a longer time.

According to the invention, the three active ingredients are dissolved or dispersed in an aqueous vehicle, advantageously sterile. The compositions according to the invention may come in liquid or solid form, for example in the form of collyriums, single-dose recipients, instillable preparations, ready-to-use or in freeze-dried form to be reconstituted with an aqueous solvent when used.

The compositions according to the invention may also come in a mixed form, for example one of the active ingredients being freeze-dried to be reconstituted by adding an aqueous solution containing the other active ingredients. It is also possible to have a bottle containing one of the solid active ingredients, covered by a frangible membrane above which can be found the solution containing the other active ingredients.

DETAILED DESCRIPTION OF THE INVENTION

The invention will be better defined using the examples below:

EXAMPLE 1

Single-Use Preparation (Strong Dose) for Intracameral Injection Prior to a Surgical Operation Tropicamide 0.00024 g
Phenylephrine (hydrochloride) 0.0038 g
Lidocaine (hydrochloride) 0.00917 g
Water for the injectable preparation in sufficient quantity for a 1-ml bottle for single use
The preparation according to the invention is to be administered by injection into the anterior chamber of the eye (intracameral zone).
Said preparation could be presented in a single packaging for easy handling with total safety, then administered to the patient in a quantity of liquid less than 1 ml, typically between 50 and 200 µl.

EXAMPLE 2

Single-Use Preparation (Usual Dose) for Intracameral Injection Prior to a Surgical Operation Tropicamide 0.00016 g
Phenylephrine (hydrochloride) 0.00258 g
Lidocaine (hydrochloride) 0.00943 g
Water for the injectable preparation in sufficient quantity for a 1-ml bottle for single use
The preparation is used under the same conditions as in example 1.

EXAMPLE 3

Collyrium without Preservatives with Tropicamide for Use Prior to a Surgical Operation Tropicamide 0.05 g
Norepinephrine (hydrochloride) 0.02 g
Lidocaine (hydrochloride) 0.12 g
Sterile purified water 10 ml
Said preparation will be presented in single-use packaging.

EXAMPLE 4

Collyrium without Preservatives for Pre-Laser Administration

Tropicamide 0.0015 g
Phenylephrine 0.030 g
Bupivacaine (hydrochloride) 0.25 g
Sterile purified water in sufficient quantity for 10 ml
Said preparation will be presented in single-use packaging.
This collyrium is particularly well suited to the treatment of pain during laser treatment.
The collyriums according to the invention are to be instilled on the eye, in three times one drop during the same day.

What is claimed is:
1. A method of preparing an eye for a medical procedure comprising the step of:
intracamerally injecting into the eye an aqueous composition comprising:

a concentration of tropicamide between 0.015 and 0.025%;
a concentration of lidocaine between 0.75 and 1.25%; and
a concentration of phenylephrine between 0.2 and 0.4%.

2. The method of claim 1, wherein a volume of the composition injected is between 0.05 and 0.2 mL.

3. The method of claim 1, wherein the pharmaceutical composition is a solution or aqueous suspension.

4. The method of claim 1, wherein the medical procedure is a cataract operation.

5. The method of claim 1, further comprising, prior to said injecting step, the step of:
reconstituting, from a freeze-dried state, at least one of said tropicamide said lidocaine and said phenylephrine in an aqueous vehicle.

6. The method of claim 1, wherein the aqueous composition comprises:
a concentration of tropicamide between 0.016% and 0.024%;
a concentration of lidocaine about 1%; and
a concentration of phenylephrine between 0.258% and 0.38%.

7. A method of preparing an eye for a medical procedure comprising the step of:
intracamerally injecting into the eye an aqueous composition comprising:
a concentration of tropicamide of about 0.024%;
a concentration of lidocaine of about 0.917%; and
a concentration of phenylephrine of about 0.38%.

8. A method of preparing an eye for a medical procedure comprising the step of:
intracamerally injecting into the eye an aqueous composition comprising:
a concentration of tropicamide of about 0.016%;
a concentration of lidocaine of about 0.943%; and
a concentration of phenylephrine of about 0.258%.

* * * * *